(12) United States Patent
Burtscher et al.

(10) Patent No.: US 9,289,359 B2
(45) Date of Patent: Mar. 22, 2016

(54) SELF-ADHESIVE MULTICOMPONENT DENTAL MATERIAL

(75) Inventors: Peter Burtscher, Rankweil (AT); Marion Eder, Dornbirn (AT); Axel Kammann, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 12/499,961

(22) Filed: Jul. 9, 2009

(65) Prior Publication Data

US 2010/0240795 A1    Sep. 23, 2010

(30) Foreign Application Priority Data

Mar. 23, 2009  (EP) ..................................... 09155935
Mar. 24, 2009  (EP) ..................................... 09156063

(51) Int. Cl.
*A61K 6/08* (2006.01)
*A61F 2/00* (2006.01)
*A61K 6/00* (2006.01)

(52) U.S. Cl.
CPC ................................... *A61K 6/0023* (2013.01)

(58) Field of Classification Search
CPC .............................. A61K 6/0023; C08L 33/00
USPC ........................................................ 523/116
See application file for complete search history.

(56) References Cited

U.S. PATENT DOCUMENTS

| | | | |
|---|---|---|---|
| 4,872,936 A | 10/1989 | Engelbrecht | |
| 6,214,101 B1 | 4/2001 | Nakaseko | |
| 6,281,271 B1 * | 8/2001 | Rumphorst et al. | 523/211 |
| 6,472,454 B1 | 10/2002 | Qian | |
| 6,583,197 B1 | 6/2003 | Wada et al. | |
| 6,732,887 B2 | 5/2004 | Bills | |
| 6,984,673 B2 | 1/2006 | Kawashima et al. | |
| 7,156,911 B2 | 1/2007 | Kangas et al. | |
| 8,129,444 B2 | 3/2012 | Hecht et al. | |
| 2002/0152930 A1 * | 10/2002 | Neubert et al. | 106/35 |
| 2003/0055123 A1 * | 3/2003 | Kawashima et al. | 523/116 |
| 2004/0235981 A1 * | 11/2004 | Qian | 523/115 |
| 2005/0014861 A1 * | 1/2005 | Qian | 523/116 |
| 2005/0252413 A1 * | 11/2005 | Kangas et al. | 106/35 |
| 2005/0252415 A1 * | 11/2005 | Budd et al. | 106/35 |
| 2005/0265931 A1 * | 12/2005 | Qian | 424/49 |
| 2006/0247330 A1 * | 11/2006 | Takano et al. | 523/116 |
| 2007/0203257 A1 * | 8/2007 | Qian | 523/116 |
| 2008/0015279 A1 * | 1/2008 | Tokui et al. | 522/182 |

FOREIGN PATENT DOCUMENTS

| | | |
|---|---|---|
| EP | 0408357 A2 | 1/1991 |
| EP | 0554890 A1 | 8/1993 |
| EP | 1269968 A1 | 1/2003 |
| EP | 1 479 364 A1 | 11/2004 |
| EP | 1 502 569 A1 | 2/2005 |
| EP | 1780223 A1 | 5/2007 |
| EP | 1878418 A1 | 1/2008 |
| EP | 2108663 A1 | 10/2009 |
| EP | 2233123 B1 | 11/2012 |
| JP | 03-045602 A | 2/1991 |
| JP | 2003-12433 A | 1/2001 |
| JP | 2003-013012 A | 1/2003 |
| JP | 200819183 | 1/2008 |
| JP | 2008-189579 A | 8/2008 |
| JP | 2008-260753 A | 10/2008 |
| WO | 02/092021 A1 | 11/2002 |
| WO | 2006/016545 A1 | 2/2006 |

OTHER PUBLICATIONS

A catalog of GC Fuji Luting S (http://www.gcdental.co.jp/sys/data/item/doc/328/), 2010.
Bollinger et al., Benzoyl Peroxide Stability in Pharmaceutical Gel Preparations, Journal of Pharmaceutical Sciences, vol. 66, No. 5, May 1977, pp. 718-722.
RelyX Unicem Clicker, RelyX Unicem Aplicap / Maxicap, Technical Product Profile, RelyX Unicem, 3M ESPE, 2007, pp. 1-60.
RelyX Unicem, Self-Adhesive Universal Resin Cement, Technical Product Profile, 3M ESPE, 2002, pp. 1-40.
RelyX Unicem, Aplicap / Maxicap, Selbstadhäsiver universaler Befestigungszement (Self-adhesive universal, Luting cement, Scientific Product Dossier), 3M ESPE, Dec. 2002.
Stawarczyk, B., et al., Effect of Surface Conditioning With Airborne-Particle Abrasion on the Tensile Strength of Polymeric CAD/CAM Crowns Luted with Self-Adhesive and Conventional Resin Cements, The Journal of Prosthetic Dentistry, Feb. 2012, pp. 94-101.
EG-Sicherheitsdatenblatt (2001/58/EG), Cristobalitmehl (EC Safety Data Sheet (2001/58/EC), Cristobalite flour), May 24, 2004, revision DE 2, pp. 1-5.
EG-Sicherheitsdatenblatt (2001/58/EG), Oberflächenmodifiziertes Cristobalitmehl (EC Safety Data Sheet (2001/58/EC), Surface-modified cristobalite flour), May 24, 2004, revision DE 2, pp. 1-5.
Quarzwerke, Stoffdaten, SIKRON—Feinstmehle Cristobalit SF3000, SF4000, SF6000, SF8000, (Quarzwerke, Material Data, SIKRON—Fine Powders, Cristobalite, SF 3000, SF4000, SF6000, SF8000), Oct. 2002, pp. 1-2.
Quarzwerke, Vorläufige Stoffdate, SILBOND 904-002, (Quarzwerke, Preliminary material data, SILBOND 904-002), Jan. 2001, pp. 1-2.

(Continued)

*Primary Examiner* — Peter F Godenschwager
*Assistant Examiner* — David Karst
(74) *Attorney, Agent, or Firm* — Ann M. Knab; Thad McMurray

(57) ABSTRACT

Curable multicomponent dental material, including a first paste, which contains (i) one or more acid group-free radically polymerizable monomers and (ii) basic filler, and a second paste, which contains (iii) one or more acid group-containing radically polymerizable monomers and (iv) non-basic filler, wherein the multicomponent dental material contains at least one initiator (v) for radical polymerization in at least paste (A) or (B).

15 Claims, No Drawings

(56) References Cited

OTHER PUBLICATIONS

Quarzwerke, Vorläufige Stoffdaten, SILMIKRON, VP 805-10/1, Cristobalit Ultrafeinstmehl, (Quarzwerke, Preliminary material data, SILMIKRON VP 805-10/1, Cristobalite ultra-fine powder), Aug. 2003, pp. 1-2.
Sicherheitsdatenblatt (91/155/EWG), Sipernat 880, (Safety Data Sheet (91/155/EWG), Sipernat 880), May 7, 2002, pp. 1-6.
Sicherheitsdatenblatt (91/155/EWG), Sipernat D 10, (Safety Data Sheet (91/155/EWG), Sipernat D 10), Nov. 4, 2002, pp. 1-6.
Tatsumori of SiO2, Fuselex Standard, extract from Tatsumori website, Aug. 28, 2013, http://www.tatsumori.co.jp/en/standard/standard_fuselex.php.

* cited by examiner

SELF-ADHESIVE MULTICOMPONENT DENTAL MATERIAL

This application claims the benefit of European Patent Application Serial No. 09155935.1, filed Mar. 23, 2009, and European Patent Application Serial No. 09156063.1, filed Mar. 24, 2009, which are hereby incorporated by reference in their entirety.

FIELD

The present invention relates to a self-bonding dental material on a paste/paste basis, preferably a fixing composite.

BACKGROUND

In dentistry, luting materials based on composites are frequently used for the cementation of dental restorations such as crowns, bridges, inlays on the hard tooth substance. By dental composites are generally meant multisubstance systems which consist of an organic monomer or polymer matrix in which one or more fillers are incorporated. For a satisfactory bond to the hard tooth substance, the luting composites are used in combination with an acid dentine adhesion promoter, i.e. before the application of the composite the hard tooth substance is treated with the acid dentine adhesion promoter.

The treatment procedure is simplified if the dentine adhesion promoter is dispensed with and the luting composite can be used alone. These so-called self-bonding or self-adhesive luting composites also contain, in the monomer matrix, acid monomers which make possible a bond to the hard tooth substance. Frequently these are dual curing systems which, in addition to a photoinitiator for light-induced curing, include an initiator system for self curing at room temperature. The self curing of the luting composite is necessary above all if the restoration to be attached (e.g. crowns, bridge) is very opaque (e.g. zirconium oxide) or even lightproof (e.g. metal).

Generally, the self-adhesive luting composites are powder/liquid-based systems which are very storage-stable as parts of the initiator system can be coated onto the powder. As powder/liquid systems are complicated to use, and require a mixer for admixing, the mixing process frequently leads, at high speeds, to inclusions of air and, with regard to the filling quantity, have no great variability, these are not among the preferred delivery forms.

A paste/paste preparation has the advantage that no special additional apparatus is required and any desired quantity of fixing material can be admixed without problems. Recently, some materials with this basis have come onto the market, but common to all is that the dentine adhesion properties of these commercially available systems fall well short of those of powder/liquid systems, and most of these paste/paste preparations display almost no dentine bonding after self curing without subsequent light curing. The known paste/paste-based luting composites also frequently cause problems of storage stability, in other words the dentine adhesion properties are no longer guaranteed after the pastes have been stored for a prolonged period.

EP 1 479 364 A1 and EP 1 502 569 A1 describe self-adhesive paste/paste dental materials which are self curing or dual curing. It was sought in these applications to improve storage stability by using special initiator systems and dividing them between the two pastes. A combination of a hydroperoxide with a specific substituted thiocarbamide is used in EP 1 479 364 A1, and in EP 1 502 569 A1 combinations of oxidants such as hydroperoxides, Cu(II), Fe(III), Co(III) salts, persulphates and permanganates with reducing agents such as e.g. sulphinates, thiocarbamide, substituted thiocarbamides, ascorbic acid and its derivatives, barbituric acid and its derivatives, thiobarbituric acid and its derivatives, Fe(II), Cu(I) and Co(II) salts are disclosed. Generally, in both applications a large number of different fillers are described without preferred fillers being highlighted, nor is the allocation of the fillers to the respective paste of the two-component system a subject of the teaching. The dentine adhesion values after curing described in EP 1 479 364 A1 and EP 1 502 569 A1 cannot be achieved in practice. In particular dentine bonding values of only 0 to 2 MPa can be achieved after storage.

SUMMARY

It is the object of the present invention to provide a self-adhesive dental material on a paste/paste basis which shows improved dentine adhesion properties, in particular even after storage, compared with known paste/paste systems.

DETAILED DESCRIPTION

The object is achieved according to the invention by a curable multicomponent dental material, including
  (A) a first paste, containing
    (i) one or more acid group-free radically polymerizable monomers and
    (ii) filler,
  (B) a second paste, containing
    (iii) one or more acid group-containing radically polymerizable monomers and
    (iv) non-basic filler,
wherein the multicomponent dental material in at least paste (A) or (B) contains at least one initiator (v) for radical polymerization.

The invention also relates to a process for the preparation of ready-to-use dental material by mixing paste (A) and paste (B) of the above-described curable multicomponent dental material.

The subject of the present invention is also an above-described curable multicomponent dental material for use in dentistry, in particular for cementation of a dental restoration to tooth enamel and/or dentine. A process is described in which paste (A) and paste (B) of the above-described curable multicomponent dental material are mixed and the obtained mixture is then applied to the hard tooth substance, i.e. tooth enamel and/or dentine.

Paste (A) of the dental material according to the invention contains (i) one or more acid group-free radically polymerizable monomers and (ii) filler, while paste (B) contains (iii) one or more acid group-containing radically polymerizable monomers and (iv) non-basic filler. Paste (A) preferably contains no acid group-containing radically polymerizable monomers, or acid group-containing radically polymerizable monomers only in a quantity of less than 1 wt.-%, preferably less than 0.5 wt.-%, and paste (B) no basic filler, or basic filler only in a quantity of less than 5 wt.-%, preferably less than 1 wt.-%, in each case relative to the total mass of the respective paste.

In a preferred embodiment, paste (B) also contains, in addition to the acid group-containing radically polymerizable monomers (iii) one or more acid group-free radically polymerizable monomers (vi). The acid group-free radically polymerizable monomers in paste (B) can be the same as or different from those in paste (A). Paste (A) contains, as filler (ii), non-basic filler, preferably basic filler or a mixture of basic filler and non-basic filler. The non-basic filler in paste (A) can be the same as or different from that in paste (B).

The multicomponent dental material according to the invention can be self curing (i.e. curing at room temperature, also called cold curing), photocurable (i.e. curing by radiation with light) and/or hot curing (i.e. curing at an increased temperature). Typically, the multicomponent dental material is self curing or dual curing, i.e. self curing and photocurable.

By a "basic filler" is meant within the meaning of the invention a filler which, if it is suspended in 50 ml distilled water (pH=7) by stirring at approx. 20° C. in a quantity of 2 g with a particle size such as is to be used in the dental material according to the invention, after 30 min raises the pH of the water to at least 8, preferably 8.5. Conversely, by a "non-basic filler" is meant herein a filler which, if it is suspended in 50 ml distilled water (pH=7) by stirring at approx. 20° C. in a quantity of 2 g with a particle size as is to be used in the dental material according to the invention, after 30 min raises the pH of the water to less than 8, preferably less than 7.5, and particularly preferably does not raise the pH, wherein a decrease in the pH is permitted.

Typical non-basic fillers which are suitable for use in paste (B) or optionally in paste (A) of the dental material according to the invention are silicon dioxide in different modifications and neutral metal salts. Preferred amongst the $SiO_2$ modifications are pyrogenic silica, precipitated silica, sol-gel silica, quartz (in particular natural quartz) and quartz glass. All $SiO_2$ modifications can be surface-treated. By surface treatment is meant both customary hydrophobing with suitable silicones, silanes and/or silazanes, e.g. hexamethyldisilazane, and also functionalization of the surface with polymerizable silanes as described below in the case of alkaline glasses. Examples of neutral metal salts include neutral fluorides of the rare-earth metals, preferably ytterbium trifluoride, but also other metal salts, such as e.g. barium sulphate, strontium fluoride, barium fluoride, yttrium fluoride and barium tungstate.

Further examples of non-basic fillers are mixed oxides of $SiO_2$ with $ZrO_2$, $Ta_2O_3$ and/or $Ta_2O_5$.

So-called "isofillers", i.e. powders which are obtained by grinding cured composites, which contain non-basic filler, which is preferably selected from the above-named non-basic fillers, are also suitable non-basic fillers. The polymer matrix of the isofiller can be prepared from different or from the same monomers which are present in the system in which it is used, but without acid group-containing monomers. It is not necessary to use in the isofiller the same filler or filler(s) of the same type as are present in the system in which the isofiller is used; for visual reasons this can, however, have advantages.

The non-basic filler can consist of a single type of non-basic filler or also of combinations of different types of non-basic fillers, preferably those named above. Particularly preferred are ytterbium trifluoride, precipitated silica, sol-gel silica, isofiller, pyrogenic silica and combinations thereof. Examples of suitable filler combinations are (a) ytterbium trifluoride, isofiller and pyrogenic silica and (b) precipitated silica (or sol-gel silica), ytterbium trifluoride and pyrogenic silica.

Preferred basic fillers which are suitable for use in paste (A) of the dental material according to the invention are alkaline glasses, e.g. silicate glasses, such as e.g. aluminosilicate glasses, aluminoborosilicate glasses, aluminum-fluorosilicate glasses, in particular glasses which contain elements of the $1^{st}$ and $2^{nd}$ main group of the periodic table of the elements, such as bariumsilicate glasses, barium-aluminum silicate glasses (e.g. including 55 wt.-% $SiO_2$, 25 wt.-% BaO, 10 wt.-% $B_2O_3$ and 10 wt.-% $Al_2O_3$), strontiumsilicate glasses, strontium-aluminiumsilicate glasses and lithium-aluminiumsilicate glasses, including in each case the corresponding fluorine-containing glasses.

The alkaline glasses can optionally be silanized. By "silanization" is meant the functionalization of the glass surface with polymerizable silanes, e.g. by reaction with (meth)acrylate-functionalized silanes, e.g. (meth)acryloyloxyalkyl-trialkoxysilanes, usually 3-(methacryloyloxy) propyltrimethoxysilane, 3-(methacryloyloxy) propyltriethoxysilane, 3-(methacryloyloxy) propyltrichlorosilane, methacryloyloxy-methyltrimethoxysilane, methacryloyloxymethyltriethoxysilane, methacryloyloxymethyltriethoxysilane, 3-(methacryloyloxy)propyl-methyldichlorosilane or 3-(meth-acryloyloxy)propylmethyldimethoxysilane. 3-(methacryloyloxy) propyltrimethoxysilane is preferred.

Isofillers as described previously, but in this case containing basic filler, preferably from those named above, are also suitable as basic filler (ii) within the meaning of the invention.

The basic filler can consist of a single type of non-basic filler or also of combinations of different types of basic fillers, preferably those named above.

The above-named non-basic and basic fillers based on quartz, quartz glass, alkaline glasses and glass ceramics are powders with a preferred weight average particle size in the range 0.01 to 10 μm, particularly preferably 0.2 to 5 μm and quite particularly preferably 0.6 to 2.0 μm. The above-named non-basic and basic fillers based on pyrogenic silica, precipitated silica, sol-gel silica and rare-earth fluorides are nanoparticulate or microfine powders with a preferred weight average particle size in the range 10 nm to 5 μm, particularly preferably 20 nm to 5 μm and quite particularly preferably 40 to 300 nm. The above-named isofillers are powders with a preferred weight average particle size in the range 3 to 100 μm, particularly preferably 3 to 20 μm and quite particularly preferably 3 to 10 μm. The above-named fillers of $SiO_2$ mixed oxides are powders with a preferred weight average particle size in the range 100 to 300 nm.

Together, the acid group-free radically polymerizable monomer(s) (i) and (vi) and acid group-containing radically polymerizable monomer(s) (iii) make the binder of the dental material according to the invention which polymerizes radically upon curing.

The acid group-free radically polymerizable monomers (i) and (vi) are preferably so-called crosslinking monomers with at least two, preferably 2 to 4, radically polymerizable groups, preferably acryloyl and methacryloyl groups. Suitable examples include 1,6-bis[2-methacryloyloxy ethoxycarbonylamino]-2,4,4-trimethylhexane (UDMA), diethylene glycol dimethacrylate, triethylene glycol dimethacrylate (TEGDMA), polyethylene glycol dimethacrylate, e.g. PEG-400-dimethacrylate, 2,2-bis[4-(2-hydroxy-3-methacryloyloxypropoxy)-phenyl]propane (Bis-GMA), 1,6-bis[2-acryloyl-oxyethoxycarbonyl-amino]-2,4,4-trimethylhexane, diethylene glycol diacrylate, triethylene glycol diacrylate, polyethylene glycol diacrylate, e.g. PEG-400-diacrylate, trimethylolpropane trimethacrylate, trimethylolpropane triacrylate, pentaerythritol tetramethacrylate, pentaerythritol tetraacrylate, propoxylated Bisphenol-A-dimethacrylate and butanediol dimethacrylate, butanediol diacrylate, 1,10-decanediol dimethacrylate ($D_3MA$), 1,10-decanediol diacrylate, 1,12-dodecanediol dimethacrylate and 1,12-dodecanediol diacrylate which are available by transesterification of (meth)acrylic acid with the corresponding di- or polyols. Hydrolysis-resistant crosslinking monomers are also suitable, for example urethanes of 2-(hydroxyl-methyl)acrylic acid and diisocyanates, such as 2,2,4-trimethylhexamethylene diisocyanate and isophorone diisocyanate; crosslinking pyrrolidones, such as e.g. 1,6-bis(3-vinyl-2-pyrrolidonyl) hexane; commercially accessible bisacrylamides or bis (meth)acrylamides, such as methylene and ethylene bisacrylamide, N,N-diethyl-1,3-bis(acrylamido)propane, 1,3-bis (methacrylamido)propane, 1,4-bis(acrylamido)butane and 1,4-bis(acryloyl)piperazine which can be synthesized by reaction from the corresponding diamines with (meth)acrylic acid chloride.

The term "hydrolysis-resistant" herein describes monomers which are stable for at least 6 weeks, i.e. hydrolyze less than 5%, in water or in mixtures of water and water-miscible solvents in a concentration of approx. 20 wt.-% and at a pH of approx. 2.0 at 37° C.

Mixtures of different crosslinking monomers are preferably used, e.g. a mixture of TEGDMA, PEG-400 dimethacrylate and UDMA, and optionally also propoxylated Bisphenol-A-dimethacrylate.

In addition to one or more crosslinking monomers, one or more so-called diluting monomers whose viscosity and good solubility make them suitable for thinning polymerization resins can also be present as acid group-free radically polymerizable monomers (i) or (vi). Diluting monomers can contain one or more polymerizable groups and in the latter case also act as crosslinking monomers.

Liquid monomers with a viscosity η of less than 100 mPa·s, measured at 20° C., are preferably used herein as diluting monomers. Examples of diluting monomers include hydrolysis-stable mono(meth)acrylates, e.g. mesitylmethacrylate; 2-(alkoxymethyl)acrylic acids, e.g. 2-(ethoxymethyl)acrylic acid, 2-(hydroxymethyl)acrylic acid; N-mono- or -disubstituted acrylamides, such as e.g. N-ethylacrylamide, N,N-dimethylacrylamide, N-(2-hydroxyethyl)acrylamide and N-methyl-N-(2-hydroxyethyl)-acrylamide or N-monosubstituted methacrylamides, such as e.g. N-ethylmethacrylamide and N-(2-hydroxyethyl)methacrylamide. Moreover, N-vinylpyrrolidone, 2-(methacryloyloxy)-ethylaceto acetate or allyl ether can be used as diluting monomers. In may cases, however, the presence of a diluting monomer is not necessary either in paste (A) or in paste (B) of the dental material according to the invention.

The acid group-containing radically polymerizable monomer(s) (iii) is (are) responsible for an improved adhesion of the dental material to enamel/dentine. These are strongly acid monomers, also called adhesive monomers, which firstly remove a small smear layer on the enamel/dentine surface when using the dental material and secondly etch the enamel or the dentine with the result that monomers can diffuse in and lead, during the following polymerization, accompanied by formation of so-called polymer tags, to a strong bond between the cured dental material and enamel/dentine.

The acid group-containing radically polymerizable monomers (iii) contain at least one ethylenically unsaturated group, preferably selected from acryloyl, methacryloyl, vinyl groups and combinations thereof, and at least one, preferably 1 to 4 acid groups. Preferred acid groups are carboxylic acid, sulphonic acid, phosphonic acid and/or phosphoric acid groups, wherein the respective partly-transesterified acid groups which still contain acidic hydrogen atoms are included. Compounds which contain phosphonic acid and/or phosphoric acid groups as acid groups are particularly preferred. Compounds with more than one acid group can contain different acid groups or preferably identical acid groups. Particularly advantageous acid group-containing radically polymerizable monomers (iii) are polymerizable dihydrogen and hydrogen phosphates.

Suitable examples of acid group-containing radically polymerizable monomers (iii) include glycerol-dimethacrylate dihydrogen phosphate (GDMP), 4-(meth)acryloyloxyethyl trimellitic anhydride, 10-methacryloyloxy decylmalonic acid, N-(2-hydroxy-3-methacryloyloxy propyl)-N-phenylglycine, 4-vinyl-benzoic acid, 2-methacryloyloxyethyl phenylhydrogen phosphate, 10-methacryloyloxydecyl dihydrogen phosphate (MDP), 2-methacryloyloxyethyl dihydrogen phosphate (HEMA phosphate), di(2-methacryloyloxyethyl) hydrogenphosphate (di-HEMA phosphate) (2-methacryloyloxypropyl dihydrogen phosphate, dipentaerythritol pentamethacryloyl oxyphosphate and phosphoric acid mono-(1-acryloyl-piperidin-4-yl)-ester. Hydrolysis-stable adhesive monomers, such as 4-vinylbenzyl phosphonic acid, 2-[4-(dihydroxyphosphoryl)-2-oxa-butyl]acrylic acid and their amides and hydrolysis-stable esters, such as e.g. 2-[4-(dihydroxyphosphoryl)-2-oxa-butyl]acrylic acid 2,4,6-trimethylphenyl ester, and (meth)acrylamide dihydrogen phosphates, such as e.g. 6-methacrylamidohexyl- and 1,3-bis (methacrylamido)-propane-2-yl-dihydrogen phosphate and 1,3-bis-(N-acryloyl-N-propyl-amino)-propane 2-yl-dihydrogen phosphate are also advantageous. Further examples include phosphonic acid monomers such as e.g. vinylphosphonic acid, 4-vinyl-phenylphosphonic acid, 2-methacryloyloxy ethylphosphonic acid, 2-methacrylamido ethylphosphonic acid, 4-methacrylamido-4-methyl-pentyl-phosphonic acid, 2-[2-dihydroxyphosphoryl)-ethoxymethyl]-acrylic acid ethyl and 2,4,6-trimethylphenyl ester. In addition, polymerizable sulphonic acids are suitable as adhesive monomers, in particular vinyl sulphonic acid, 4-vinylphenyl sulphonic acid or 3-(methacrylamido)propyl sulphonic acid.

The curable multicomponent dental material according to the invention contains in paste (A) and/or paste (B) at least one initiator (v) for radical polymerization. This means that the dental material according to the invention can also contain different initiators which are then present either in the same paste or in different pastes. The initiator for radical polymerization is selected depending on whether hot curing and/or self curing and/or radiation curing is desired for the dental material according to the invention. In preferred embodiments the dental material according to the invention is self curing and in particularly preferred embodiments dual curing, i.e. self curing and photochemically curable. By radiation curing is meant preferably curing by visible light, in particular blue light with a wavelength of 300 to 550 nm, preferably 400 to 500 nm.

Benzopinacol, 2,2'-dialkylbenzopinacols and peroxides, in particular benzoylperoxide, for example are suitable as initiators for hot curing.

For self curing, these initiators are combined with a suitable activator (vii). A peroxide, in particular benzoylperoxide, is preferably used as initiator (v) for self curing. In this case, a basic activator, preferably a reducing amine, particularly preferably an aromatic amine, such as e.g. N,N-dimethyl-sym.-xylidine or N,N-dimethyl-p-toluidine, serves as activator (vii). In addition, redox systems consisting of peroxides and reducing agents, such as e.g. ascorbic acid, barbiturates or sulphinic acids, are also suitable as an initiator/activator combination for self curing. It is self-evident that the initiator (v) and the activator (vii) must be present in different pastes in order to prevent an undesired premature polymerization. If an initiator/activator combination with a basic activator, such as e.g. benzoyl-peroxide/aromatic amine is used, then the activator (vii) is introduced into paste (A) and the initiator (v) into paste (B).

Examples of suitable photoinitiators (viii) include benzophenone, benzoin and derivatives thereof and α-diketones and derivatives thereof, such as 9,10-phenanthrenequinone, 1-phenyl-propane-1,2-dione, diacetyl and 4,4'-dichlorobenzil. Acyl phosphinic oxides, such as e.g., 2,4,6-trimethylbenzoyl diphenylphosphinic oxide, and bisacylphosphinic oxides, such as e.g., bis(2,4,6-trimethylbenzoyl)phenylphosphinic oxide, are also suitable. Camphorquinone, 2,2-methoxy-2-phenyl-acetophenone or α-diketones each in combination with an activator in the form of a reduced amine, such as e.g. 4-(dimethylamino)benzoic acid ester, N,N-dimethylamino ethylmethacrylate, N,N-dimethyl-sym.-xylidine or triethanolamine are preferred. Further suitable photoinitiators are monobenzoyl or dibenzoylgermanium derivatives.

For dual curing, an initiator/activator combination for self curing is combined with a photoinitiator. In this case also a common activator can be used for both the initiator for self curing and also for the photoinitiator.

The photoinitiator (viii) can be present in paste (A) or (B). If a basic activator, e.g. an amine, is used for photoinitiator (viii), then the activator (vii) is introduced into paste (A). Because there is no need with a light-activated initiator system to separate initiator and activator, initiator and activator can be introduced in the same or different pastes. The photoinitiator is preferably located in paste (A).

The dental material according to the invention preferably does not contain an added solvent.

The multicomponent dental material of the present invention is typically a 2-component dental material. Thus it is preferably a 2-component dental material on a paste/paste basis.

By paste is meant herein a solid-liquid mixture (suspension) with a high solids content. Pastes are no longer free-flowing, but resistant to spreading. They have a dough-like consistency.

Paste (A) of the dental material according to the invention preferably has a filler content of 40 to 90 wt.-%, particularly preferably 60 to 85 wt.-%, quite particularly preferably 65 to 80 wt.-% and most preferably 70 to 80 wt.-%, relative in each case to the total mass of paste (A). The percentage by weight of the non-basic filler in the overall filler is preferably less than 50%, more preferably less than 30%.

Paste (B) of the dental material according to the invention preferably has a filler content of 40 to 90 wt.-%, particularly preferably 60 to 85 wt.-%, and quite particularly preferably 60 to 70 wt.-%, relative in each case to the total mass of paste (B).

The part of the pastes (A) and (B) which is not filler is called matrix mixture below. The matrix mixtures of pastes (A) and (B) include the radically polymerizable monomers and optionally initiator(s), activator(s) and further optional components.

The matrix mixture of paste (A) contains acid group-free radically polymerizable monomers (i) in a total quantity of preferably 88 to 100 wt.-%, in particular 88 to 99.93 wt.-%, particularly preferably 94 to 99.85 wt.-% and quite particularly preferably 94.9 to 99.7 wt.-%, relative in each case to the mass of the matrix mixture of paste (A). The matrix mixture of paste (A) preferably contains activator in a total quantity of 0.05 to 10 wt.-%, preferably 0.1 to 5.0 wt.-% and particularly preferably 0.2 to 4.5 wt.-%, relative in each case to the mass of the matrix mixture of paste (A). The matrix mixture of paste (A) preferably contains photoinitiator in a quantity of 0.02 to 2.0 wt.-%, preferably 0.05 to 1.0 wt.-% and particularly preferably 0.1 to 0.6 wt.-%, relative in each case to the mass of the matrix mixture of paste (A).

The matrix mixture of paste (B) can contain as binder exclusively acid group-containing radically polymerizable monomer. Paste (B) preferably contains acid group-containing radically polymerizable monomers (i) in a total quantity of 3 to 40 wt.-%, particularly preferably 4 to 30 wt.-%, and quite particularly preferably 5 to 15 wt.-%, relative in each case to the mass of the matrix mixture of paste (B). The matrix mixture of paste (B) preferably contains the optional acid group-free radically polymerizable monomers (vi) in a total quantity of 60 to 96.7 wt.-%, particularly preferably 70 to 95.95 wt.-% and quite particularly preferably 85 to 94.9 wt.-%. The matrix mixture of paste (B) preferably contains initiator (v) for self curing in a quantity of 0.3 to 5 wt.-%, preferably 0.7 to 3 wt.-% and particularly preferably 1.0 to 2.0 wt.-%, relative in each case to the mass of the matrix mixture of paste (B). Optionally the matrix mixture of paste (B) can in addition or alternatively to the initiator for self curing contain photoinitiator (viii) in a quantity of 0.02 to 2.0 wt.-%, preferably 0.05 to 1.0 wt.-% and particularly preferably 0.1 to 0.6 wt.-%, relative in each case to the mass of the matrix mixture of paste (B).

A preferred embodiment relates to a dental material in which paste (A):
  contains 65 to 80 wt.-%, particularly preferably 70 to 80 wt.-%, filler selected from basic filler (ii) and a combination of basic filler (ii) and non-basic filler (ix) and
  20 to 35 wt.-%, particularly preferably 20 to 30 wt.-%, of the above-defined matrix mixture for paste (A), relative in each case to the total mass of paste (A), and
paste (B):
  contains 60 to 70 wt.-% non-basic filler (iv),
  30 to 40 wt.-% of the above-defined matrix mixture for paste (B),
  relative in each case to the total mass of paste (B).

A ready-to-use dental material can be prepared from the multicomponent dental material of the present invention by simple mixing of pastes (A) and (B). The mixing can take place e.g. by hand, e.g. with a spatula on a mixing block. Alternatively, the two pastes (A) and (B) can also be introduced into a double syringe, in order then to be mixed automatically with an automatic mixing cannula during use. The mixing of the pastes (A) and (B) preferably takes place in a volume ratio in the range of 0.4:0.6 to 0.6:0.4, particularly preferably in the range of 0.43:0.57 to 0.57:0.43, quite particularly preferably in the range of 0.46:0.54 to 0.54:0.46 and most preferably in a volume ratio of approx. 1:1. The dental material according to the invention can be used as a luting composite, e.g. for the cementation of crowns, bridges, root pins and inlays. The dental material according to the invention is self-adhesive, i.e. it can be applied direct to the hard tooth substance without using an adhesion promoter.

The dental material according to the invention is applied for example as follows: The hard tooth substance is rinsed after preparation and lightly blown dry. The dental material according to the invention is added to the bonding surface of the restoration immediately after mixing and the restoration placed on the tooth. Any excesses which occur are polymerized by being exposed to a polymerization lamp and removed. In the case of a lightproof restoration this is pressed fast to the tooth until curing takes place (e.g. for at least 1, 2 or 3 minutes). In the case of transparent restorations this can be exposed to a polymerization lamp through the restoration and the dental material can thus be light cured, e.g. with exposure times of 10 to 30 s per side, preferably approx. 20 s per side.

It was surprisingly established that, because of the distribution according to the invention of the basic and non-basic fillers between the individual pastes of the multicomponent system, a clear improvement in the dentine adhesion of the cured dental material compared with known self-adhesive paste/paste systems is achieved. The self-adhesive dental material according to the invention typically has a dentine adhesion after self curing at room temperature of at least 4 MPa, preferably at least 5 MPa and particularly preferably at least 6.5 MPa and after photocuring of at least 7 MPa, preferably at least 8 MPa and particularly preferably at least 9.5 MPa.

It was surprisingly found that the interaction between filler and acid matrix plays a decisive role for a functioning self-adhesive composite on a paste/paste basis. In composites of the state of the art, in which basic fillers are present in an acid monomer matrix, the interaction of the acid adhesive monomers with the basic filler is seemingly strong enough to bring about an at least partial deactivation of the acid monomers, with the result that these can no longer etch the hard tooth substance to the necessary degree, and the dentine adhesion is reduced. Non-basic fillers according to the invention are therefore fillers which engage in no, or only very small, interactions with the acid monomers. With the present invention, there is preferably no interaction of the acid group-containing radically polymerizable monomers (iii) with the non-basic filler (iv). As an interaction between filler and acid monomer is avoided, the multicomponent dental material according to the invention has a very good storage stability, i.e. its dentine adhesion remains very good even after storage.

In the case of phosphorous-containing acid monomers, i.e. those with phosphoric acid or phosphonic acid groups, the interaction can be demonstrated by $^{31}P$ spectroscopy. For this, $CDCl_3$ is added to the freshly produced paste (paste: $CDCl_3$ mixing ratio=1:1), and the mixture stirred and centrifuged. A $^{31}P$-NMR spectrum is recorded with the supernatant solution. If there is no interaction between acid matrix and filler, a strong signal, at approx. −1-2 ppm in the case of phosphoric acid monoesters and diesters and −30 ppm in the case of organophosphonic acids and organophosphonic acid monoesters is obtained which corresponds to the signal of the pure phosphorous-containing compound. Interactions between filler and acid matrix result in a broadening of the peak compared with the signal of the pure phosphorous-containing compound. Any filler which does not bring about a broadening of the peak is a suitable non-basic filler (iv) within the meaning of the present invention.

The invention is described in further detail below with reference to examples. The percentages are in each case percentages by weight.

EXAMPLES

The pastes of Examples 1 and 2 with the compositions indicated below were prepared as follows. Unless otherwise stated, all values are by weight (parts by weight). Firstly the matrix mixtures were prepared by stirring the individual monomers together. Initiator and where applicable activator were dissolved in the monomer mixture. The matrix mixtures were introduced into a stirrer and the fillers stirred in until homogeneous pastes were present. To determine the dentine adhesion, the prepared pastes (A) and (B) of Examples 1 and 2 were each mixed 1:1 (as the density of the two pastes was roughly identical, a 1:1 volume ratio corresponded here to roughly a 1:1 weight ratio).

Measuring the Adhesion to Dentine and Enamel

The adhesion to the hard tooth substance was carried out using the so-called Ultradent method. For this, bovine teeth were embedded in polyester resin. Depending on whether the adhesion to enamel or dentine were to be examined, the uppermost enamel layer was ground with 120 grid sandpaper under water and reground with 600 grid sandpaper under water. In the case of dentine adhesion, grinding with 120 grid sandpaper took place until the dentine surface was exposed. Before preparing the testpiece for the adhesion examination, the tooth surface was rinsed with water and lightly dried with an air blower, but not blown dry. A prepolymerized composite block comprising Tetric EvoCeram (light curing precipitation material from Ivoclar Vivadent AG, Liechtenstein) 3 mm long and 2.3 mm in diameter was prepared by radiation (20 seconds) with a dental polymerization lamp (Bluephase, Ivoclar Vivadent AG, 400-500 nm). The moulded body was then coated on the adhesion surface with little fixing composite and placed on the dentine surface. The composite testpiece was fixed to the tooth surface by means of a screw and the excess cement removed.

To determine the dentine or enamel adhesion after self curing, the testpiece array was stored for 15 minutes at 37° C. in the drying oven; to determine the adhesion after light curing the cement seam was lit by a polymerization lamp (Bluephase, Ivoclar Vivadent AG) for 20 seconds after removal of the excess cement. The bodies were demoulded (released from the screw fixing) and stored in water at 37° C. After 24 hours the composite testpiece was cut off from the tooth surface with a cross-head speed of 0.8 mm/min. A series of measurements covered 8 testpieces, wherein the average and the standard deviation were calculated.

Example 1

Paste (A)

| Proportion | Component |
|---|---|
| 25.0% | Matrix mixture of paste (A) |
| 71.4% | Barium-aluminium-fluorosilicate glass filler G018-056*) 7 μm (Schott AG, Mainz; weight average particle diameter 7 μm); approx. 5% silane**) |
| 2.1% | Barium-aluminium-fluorosilicate glass filler G018-056*) 1 μm (Schott AG, Mainz; weight average particle diameter 1 μm); approx. 5% silane**) |
| 1.5% | Pyrogenic silica HDK ® H2000 (Wacker Chemie AG, Munich; hydrophobized by surface modification with trimethylsiloxy, BET surface area of 170-230 m²/g) |

*)24% $SiO_2$, 23% $Al_2O_3$, 2% $Na_2O$, 15% CaO, 8% $P_2O_5$, 11% BaO, 17% F
**)94% filler, 5% silane and 1% water are mixed and evaporated after the reaction of non-reacted silane Matrix Mixture of Paste (A):

| Proportion | Component |
|---|---|
| 34.0% | TEGDMA (Triethylene glycol dimethacrylate) |
| 10.0% | PEG-400 dimethacrylate |
| 51.6% | UDMA (1,6-bis[2-methacryloyl-oxyethoxycarbonyl-amino]-2,4,4-trimethyl hexane) |
| 0.3% | Camphorquinone |
| 0.6% | 4-(dimethylamino) benzoic acid ethyl ester |
| 3.5% | N,N-Dimethyl-sym.-xylidine |

Paste (B)

| Proportion | Component |
|---|---|
| 35.0% | Matrix mixture of paste (B) |
| 24.5% | Isofiller of monomer, pyrogenic silica and ytterbium fluoride* |

-continued

| | |
|---|---|
| 39.0% | Ytterbium fluoride (particle size 200 nm) |
| 1.5% | Pyrogenic silica HDK ® H2000 |

*The isofiller was prepared from a composite of:
30% Matrix mixture of
    78.5% UDMA
    21.0% Decanediol dimethacrylate
    0.5% Benzoylperoxide
50% Pyrogenic silica Aerosil ® OX-50 (Evonik Degussa; particle size 40 nm)
10% Ytterbium trifluoride
by polymerizing the composite into cakes (thickness 1 cm) at 100° C. for approx. 2 hours and then grinding the latter (average particle size after grinding 5 μm)

Matrix Mixture of Paste (B):

| Proportion | Component |
|---|---|
| 10.0% | MDP (10-methacryloyloxydecyl dihydrogen phosphate) |
| 30.0% | TEGDMA |
| 8.0% | PEG 400 dimethacrylate |
| 50.5% | UDMA |
| 1.5% | Benzoylperoxide |

Dentine Adhesion:
After self curing: 8.2±1.8 Mpa
After light curing: 12.0±2.0 MPa Example 2

Paste (A)

| Proportion | Component |
|---|---|
| 25.0% | Matrix mixture of paste (A) |
| 71.4% | Barium-aluminium-fluorosilicate glass filler G018-056 7 μm (as per Example 1) |
| 2.1% | Barium-aluminium-fluorosilicate glass filler G018-056 1 μm (as per Example 1) |
| 1.5% | Pyrogenic silica HDK ® H2000 |

Matrix Mixture of Paste (A):

| Proportion | Component |
|---|---|
| 34.0% | TEGDMA |
| 10.0% | PEG 400 dimethacrylate |
| 51.6% | UDMA |
| 0.3% | Camphorquinone |
| 0.6% | 4-(Dimethylamino)-benzoic acid ethyl ester |
| 3.5% | N,N-Dimethyl-sym.-xylidine |

Paste (B)

| Proportion | Component |
|---|---|
| 40.4% | Matrix mixture of paste (B) |
| 45.3% | Sol-gel silica ("Sunspheres" from Asahi Glass Co., Ltd, average particle size 200 nm) |
| 12.6% | Ytterbium fluoride |
| 1.7% | Pyrogenic silica HDK ® H2000 |

Matrix Mixture of Paste (B):

| Proportion | Component |
|---|---|
| 10.0% | MDP |
| 22.8% | TEGDMA |
| 7.6% | PEG 400 dimethacrylate |
| 33.7% | Propoxylated Bisphenol-A dimethacrylate |
| 24.4% | UDMA |
| 1.5% | Benzoylperoxide |

Dentine Adhesion:
After self curing: 7.2±2.0 Mpa
After light curing: 10.2±2.7 MPa Even after storage over a period of 2 months, the pastes of Examples 1 and 2 still showed very good dentine adhesion values. The measurement values achieved after storage of the pastes from Example 2 at room temperature or at 37° C. are shown in the following tables.

Storage at Room Temperature:

| Storage time | Self curing (MPa) | Light curing (MPa) |
|---|---|---|
| Initial | 7.7 ± 2.1 | 10.8 ± 2.9 |
| 1 month | 10.1 + 1.6 | 10.3 ± 2.0 |
| 2 months | 9.2 + 1.1 | 11.3 ± 2.3 |
| 3 months | 9.3 ± 1.4 | 11.2 ± 3.5 |

The data at room temperature are constant and do not show any impairment.

Storage at 37° C.:

| Storage time | Self curing (MPa): | Light curing (MPa) |
|---|---|---|
| Initial | 7.7 ± 2.1 | 10.8 ± 2.9 |
| 4 weeks | 8.3 ± 2.0 | 11.2 ± 1.9 |
| 6 weeks | 9.6 ± 1.3 | 9.1 ± 3.3 |

Example 3

Comparison Example

The dentine adhesion of the fixing composite Maxcem Elite™ from Kerr Corporation, USA, was examined as described above. As far as the inventors of the present application are aware, Maxcem Elite™ has the following composition:

Paste 1
Filler content 77%
Filler Composition:

| Filler | Percentage by weight |
|---|---|
| $Al_2O_3$ | 9.6% |
| $SiO_2$ | 59.2% |
| BaO | 31.2% |

Matrix Mixture:

| Component | Percentage by weight |
|---|---|
| Glycerol phosphoric acid dimethacrylate | 69% |
| Pentaerythritol tetraacrylate | 9.7% |

-continued

| Component | Percentage by weight |
| --- | --- |
| Bis-GMA | 16.4% |
| Unidentifiable proportions | 4.9% |

Paste 2
Filler content 77%
Filler Composition:

| Filler | Percentage by weight |
| --- | --- |
| F | 14.9% |
| $Al_2O_3$ | 19.0% |
| $SiO_2$ | 26.,% |
| ZnO | 11.7% |
| SrO | 22.8% |
| $ZrO_2$ | 4.9% |

Matrix Mixture:

| Component | Percentage by weight |
| --- | --- |
| UDMA | 73.6% |
| Glycerol dimethacrylate | 23.8% |
| 4-(dimethylamino) benzoic acid ethyl ester | 1% |
| Unidentifiable proportions | 1.6% |

Dentine Adhesion:
After self curing: 2-4 Mpa
After light curing: 1-6 MPa

The clearly poorer dentine adhesion values of the Comparison Example 3 are attributable to the fact that here the paste 1 simultaneously contains, in contrast to the teaching according to the invention, in addition to the acid monomer glycerol phosphoric acid dimethacrylate, the basic filler barium-aluminumsilicate glass.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. Curable multicomponent dental material, comprising
   (A) a first paste, containing
      (i) one or more acid group-free radically polymerizable monomers,
      (ii) a basic filler,
      (vii) a basic activator,
      (viii) a photoinitiator which comprises camphorquinone, and
      (ix) a non-basic filler which is selected from $SiO_2$, neutral metal salts and their combinations,
   (B) a second paste, containing
      (iii) one or more acid group-containing radically polymerizable monomers which comprises at least one phosphonic acid group and/or phosphoric acid group,
      (iv) non-basic filler,
      (v) an initiator which contains peroxide,
      (vi) one or more acid group-free radically polymerizable monomers and
   wherein the dental material does not contain an added solvent,
   wherein paste (A) does not contain acid group-containing radically polymerizable monomers and paste (B) does not contain basic filler, and
   wherein the non-basic filler (iv) does not cause a broadening of a $^{31}P$ peak of the acidic monomer (iii) in a $^{31}P$-NMR spectrum of monomer (iii).

2. Dental material according to claim 1, in which the non-basic filler (iv) is selected from $SiO_2$, neutral metal salts and their combinations.

3. Dental material according to claim 2, in which the non-basic filler (iv) is selected from quartz, pyrogenic silica, precipitated silica, sol-gel silica, quartz glass, neutral fluorides of rare-earth metals, and their combinations.

4. Dental material according to claim 3, which comprises ytterbium trifluoride.

5. Dental material according to claim 1, in which the at least one acid group-containing radically polymerizable monomer (iii) contains at least one ethylenically unsaturated group, selected from acryloyl, methacryloyl, vinyl groups and their combinations, and at least one acid group, selected from phosphonic acid, phosphoric acid groups and their combinations.

6. Dental material according to claim 5, in which the at least one acid group-containing radically polymerizable monomer (iii) is a radically polymerizable dihydrogen or hydrogenphosphate.

7. Dental material according to claim 1, which contains at least one acid group-free radically polymerizable monomer (i), which has at least two ethylenically unsaturated groups.

8. Dental material according to claim 7, wherein the ethylenically unsaturated groups are selected from acryloyl and methacryloyl groups.

9. Process for the preparation of a ready-to-use dental material comprising mixing paste (A) and paste (B) of the curable multicomponent dental material according to claim 1, in a volume ratio in the range 0.4:0.6 to 0.6:0.4.

10. The process according to claim 9, wherein the volume ratio is in the range 0.46:0.54 to 0.54:0.46.

11. Double syringe with a first and second reservoir, comprising a curable multicomponent dental material according to claim 1, wherein paste (A) is contained in the first reservoir and paste (B) in the second reservoir.

12. Dental material according to claim 1, wherein the peroxide is benzoylperoxide and the basic activator is an aromatic amine.

13. Dental material according to claim 1, in which the non-basic filler (ix) is selected from quartz, pyrogenic silica, precipitated silica, sol-gel silica, quartz glass, neutral fluorides of rare-earth metals, and their combinations.

14. Dental material according to claim 1, which contains at least one acid group-free radically polymerizable monomer (vi), which has at least two ethylenically unsaturated groups.

15. Dental material according to claim 1, which contains barium-aluminium silicate glass filler in paste (A).

* * * * *